United States Patent
Kang et al.

(10) Patent No.: US 7,399,976 B2
(45) Date of Patent: Jul. 15, 2008

(54) METHOD AND EQUIPMENT FOR DISCRIMINATING MATERIALS BY EMPLOYING FAST NEUTRON AND CONTINUOUS SPECTRAL X-RAY

(75) Inventors: Kejun Kang, Beijing (CN); Haifeng Hu, Beijing (CN); Yali Xie, Beijing (CN); Qitian Miao, Beijing (CN); Yigang Yang, Beijing (CN); Yuanjing Li, Beijing (CN); Zhiqiang Chen, Beijing (CN); Xuewu Wang, Beijing (CN)

(73) Assignees: Tsinghua University, Beijing, P.R. (CN); Nuctech Company Limited, Beijing, P.R. (CN)

( * ) Notice: Subject to any disclaimer, the term of this patent is extended or adjusted under 35 U.S.C. 154(b) by 5 days.

(21) Appl. No.: 11/353,472

(22) Filed: Feb. 14, 2006

(65) Prior Publication Data

US 2007/0096036 A1  May 3, 2007

(30) Foreign Application Priority Data

Nov. 3, 2005 (CN) ........................ 2005 1 0086764

(51) Int. Cl.
*G01N 23/02* (2006.01)
(52) U.S. Cl. ................................. 250/390.04
(58) Field of Classification Search ............. 250/390.04
See application file for complete search history.

(56) References Cited

U.S. PATENT DOCUMENTS 5,838,759 A * 11/1998 Armistead .................. 378/57

2004/0109532 A1 * 6/2004 Ford et al. .................... 378/57

FOREIGN PATENT DOCUMENTS

WO   WO 98/55851   12/1998
WO   WO 2004/053472   6/2004

* cited by examiner

*Primary Examiner*—Constantine Hannaher
*Assistant Examiner*—Marcus H Taningco
(74) *Attorney, Agent, or Firm*—Westerman, Champlin & Kelly, P.A.

(57) ABSTRACT

Disclosed is a method of discriminating materials by employing fast neutron and continuous spectral X-ray and an equipment for the same. The method comprising the steps of: (a) transmitting a fast neutron beam produced by a fast neutron source and a continuous spectral X-ray beam produced by a continuous spectral X-ray source through inspected objects; (b) directly measuring the intensity of the transmitted X-rays and the intensity of the transmitted neutrons by a X-ray detector array and a neutron detector array respectively; and (c) identifying the materials of the inspected object by Z-dependency curves formed by the attenuation differences between the neutron beam and X-ray beam transmitted through different materials of the inspected object. This direct measurement of transmitted dual-ray technique has much more efficient than secondary radiations measurement such as neutron activation analysis, has much more material discrimination sensitivity than dual-energy x-ray technique. The respective measurements of neutrons and x-rays make the usages of high detect efficiency neutron detectors and x-ray detectors possible. The using continuous spectral x-ray produced by Linac adds more advantages such as: high penetration ability, high spatial resolution, and high image quality over monoenergetic dual-ray technique.

25 Claims, 3 Drawing Sheets

METHOD AND EQUIPMENT FOR DISCRIMINATING MATERIALS BY EMPLOYING FAST NEUTRON AND CONTINUOUS SPECTRAL X-RAY

The present application claims priority of Chinese patent application Serial No. 200510086764.8, filed Nov. 3, 2005, the content of which is hereby incorporated by reference in its entirety.

FIELD OF THE INVENTION

This invention relates to a radiographic technique for containers and other voluminous objects inspection, especially to an equipment and method for discriminating materials by directly measuring the transmitted fast neutrons and continuous spectral x-rays and identifying materials by employing the Z-dependency curves formed by the attenuations differences between neutrons and x-rays transmitted through different materials.

BACKGROUND OF THE INVENTION

The present invention is driven by the global terrorism threat. As the antiterrorism situation getting severe, the radiographic container inspection systems capable of automatically detecting explosive, drugs and other contraband become pressing desired. The existing material discrimination techniques for container and other voluminous objects inspection, such as: high and dual energy radiographic technique, PFNA and container inspection CT, show more and more important.

High and dual energy radiographic technique employs absorption variation between materials in the megavolt range due to the Compton Effect and Pair Production Effect to determine the effective atomic number of the irradiated objects, and accordingly to discriminate different materials. But there are some physical limitations: First, absorption variation is not big enough. Second, the high-energy spectrum partially overlapped with low energy spectrum, even with spectrum filtering only can solve part of problems. Third, measurement error degrades the discrimination effect. All this factors make the unsatisfied results, and sequentially high and dual energy system mainly used to identify "organic", "compound" and "inorganic" material in inspected container. Isotope source can provide monoenergetic gamma-ray which can solve the spectrum overlap problem, but penetration ability is too low to be used in container and other voluminous objects inspection system for material discrimination.

Present available PFNA systems, some have 3D material discriminating ability. But their spatial resolution is too big, throughput is too slow, and the price is too high. So PFNA can't dominate container inspection market at present and near future. Some NAA container inspection system using Cf-252 as neutron source can't be used for on-line real-time measurement, because only after the suspicious area having been detected by other equipment, the NAA measurement for suspicious area can be performed.

Container inspection CT system is giant and the throughput rate is too low to dominate container inspection market.

WO 2004/053472 discloses a radiographic equipment which directly measure transmitted monoenergetic fast neutron and monoenergetic gamma-ray. This equipment employs mass attenuation coefficient ratio to discriminate different materials, which can be used for detecting explosives, drugs and contraband. Comparing with high and dual energy X-ray technique, the direct measuring transmitted dual-ray technique has better material identification ability. Comparing with PFNA technique which measures secondary radiations such as neutron-induced gamma rays, the direct measuring transmitted dual-ray technique has much more efficient, especially has high penetration ability than thermal neutron. Comparing with container inspection CT, the dual-ray system is compact, low price and real-time measurement.

Unfortunately, the monoenergetic dual-ray system only can use isotope source, such as Co-60, as its gamma-ray source. Nevertheless, for containers or other voluminous objects inspection, the big disadvantage of isotope source is low penetration ability, low spatial resolution, poor image quality, and has radiation safety administration problems. This technique only provides low spatial resolution container transmission image, so is difficult to compete with Linac container inspection systems which provide high quality image. Since monoenergetic gamma-ray has low penetration ability, which limits its material identifying thickness as well, can't be used in case of fully-loaded container or thick objects inspection. All those defects limit its applications.

SUMMARY OF THE INVENTION

The present invention has solved above problems and provides material discrimination methods and equipments by directly measuring transmitted fast neutron and continuous spectral X-ray. Since the mass attenuation coefficient ratio of fast neutron and continuous spectral X-ray can't be simply used to determine Z (Line-of-Sight Effective Atomic Number of inspected objects), the present invention employs Z-dependence n-x curves to do material identification. Take advantage of high penetration ability of Linac X-ray and fast neutrons, it can do material identification well even in the cases of fully-load container or thick objects. This invention not only has all the advantages of monoenegetic dual-ray system such as: high material discriminating sensitivity, compact configuration, high throughput, low price, real-time measurement, but also has the added advantages such as: high penetration ability, high detect efficiency, high spatial resolution, high image quality, high material identification precision and veracity.

According to one aspect of the invention, a method of discriminating materials by employing fast neutron and continuous spectral X-ray comprising the steps of: (a) transmitting a fast neutron beam produced by a fast neutron source and a continuous spectral X-ray beam produced by a continuous spectral X-ray source through inspected object; (b) directly measuring the intensity of the transmitted X-rays and the intensity of the transmitted neutrons by an X-ray detector array and a neutron detector array respectively; and (c) identifying the materials of the inspected object by Z-dependency curves formed by the attenuation differences between the neutron beam and the X-ray beam transmitted through different materials of the inspected object.

In a preferred embodiment of the invention, the method further comprising a step of: (d) forming 2-dimensional X-ray transmission image and neutron transmission image at same scan.

In a preferred embodiment of the invention, the fast neutron source is one of a neutron generator, an isotope neutron source and a photoneutron source; and the continuous spectral X-ray source is one of an electron linear accelerator and an X-ray machine.

In a preferred embodiment of the invention, the photoneutron source is an accelerator for producing an X-ray beam part of which impinges on photoneutron converter and is converted into photoneutrons.

In a preferred embodiment of the invention, a distribution collimator divides the X-ray beam produced by the accelerator into two beams, one beam is collimated by X-ray beam-limited collimator so as to form an X-ray beam, the other beam impinges on photoneutron converter and is converted into photoneutrons to form a photoneutron beam by beam-limited collimator.

In a preferred embodiment of the invention, the fast neutron beam and the continuous spectral X-ray beam are measured by an X-ray detector array having high X-ray detecting efficiency and a neutron detector array having high neutron detecting efficiency respectively.

In a preferred embodiment of the invention, along the scanning tunnel a neutron scanner frame comprising the fast neutron source and the neutron detector array is located in parallel with an X-ray scanner frame comprising the X-ray source and the X-ray detector array; and along the direction of scanning, the X-ray scanner frame is preceding and the neutron scanner frame is behind so that the inspected object is scanned by X-ray scanner frame first, and then scanned by neutron scanner frame.

In a preferred embodiment of the invention, the neutron source and the X-ray source are pulsed in synchronism, and the emitting time of pulse neutron source is delayed a period of time, for example several milliseconds, from the emitting time of the pulse X-ray source.

In a preferred embodiment of the invention, wherein the identifying of the materials comprising: measuring the intensity $T_n$, of neutron transmitted through the inspected object by every neutron detector of the neutron detector array; measuring the intensity $T_x$ of X-ray transmitted through the inspected object by every X-ray detector in the X-ray detector array; composing Z-dependence curves by the pairs of $(c_1, c_2)$, wherein $c_1 = f_1(T_x)$ is used as x-coordinator and $c_2 = f_2(T_n, T_x)$ is used as y-coordinator, wherein $f_1(T_x)$ denotes a function of the attenuation of X-ray, and $f_2(T_n, T_x)$ denotes a function of the attenuation difference of neutron and X-ray; identifying the different materials of the inspected object by using the Z-dependence curves; and displaying the identified different materials by different colors in an material discrimination image.

In a preferred embodiment of the invention, one pixel value of the neutron transmission image is paired with the mean of one or several pixels value of the X-ray transmission image to compose a $(c_1, c_2)$ pair on one of the Z-dependence curves.

In a preferred embodiment of the invention, there are two scanning models for forming the X-ray transmission image and the neutron transmission image, one is a neutron scanner frame and an X-ray scanner frame moving, while the inspected object holds still; the other is the inspected object moving along the scanning tunnel, while the neutron scanner frame and the X-ray scanner frame are stationary.

In another aspect of the invention, an equipment for performing the method for discriminating materials by employing fast neutron and continuous spectral X-ray, comprising: a fast neutron source for producing neutrons; a continuous spectral X-ray source for producing X-rays; a neutron detector array for detecting the neutrons; and an X-ray detector array for detecting the X-rays; wherein the fast neutron source and the continuous spectral X-ray source are located at one side of a scanning tunnel, and the neutron detector array and the X-ray detector array are located at opposite side of the scanning tunnel.

In a preferred embodiment of the invention, the X-rays produced by the X-ray source are collimated into an X-ray beam which aims at the X-ray detector array, the X-ray beam transmits through the inspected object, and is received by the X-ray detector array; the neutrons produced by the fast neutron source are collimated into a neutron beam which aims at the neutron detector array, the neutron beam transmits through the inspected object, and is received by the neutron detector array.

In a preferred embodiment of the invention, the fast neutron source is one of a neutron generator, an isotope neutron source and a photoneutron source; and the continuous spectral X-ray source is one of an electron linear accelerator and an X-ray machine.

In a preferred embodiment of the invention, along the scanning tunnel, a neutron scanner frame comprising the fast neutron source and the neutron detector array is located in parallel with an X-ray scanner frame comprising the X-ray source and the X-ray detector array.

In a preferred embodiment of the invention, along the direction of scanning, the X-ray scanner frame is preceding, the neutron scanner frame is behind so that the inspected object is scanned by the X-ray scanner frame first, and then scanned by the neutron scanner frame.

In still another aspect of the invention, an equipment for performing the method for discriminating materials, comprising: an accelerator producing continuous spectral X-rays and photoneutrons; a neutron detector array for detecting photoneutrons; and an X-ray detector array for detecting X-rays; wherein the accelerator is located at one side of a scanning tunnel, the neutron detector array and the X-ray detector array are located at the other side of the scanning tunnel.

In a preferred embodiment of the invention, the equipment further comprising: an X-ray distribution collimator, which is installed at an X-ray beam emitting window of the accelerator, and divides the X-ray beam into two beams, one beam is collimated by the X-ray beam-limited collimator so as to form an X-ray beam, the other beam is collimated and leaded into a photoneutron enhancement chamber.

In a preferred embodiment of the invention, the equipment further comprising: a photoneutron converter, which is placed in the photoneutron enhancement chamber, and is interposed in the path of the X-ray beam, the X-ray beam impinges on the photoneutron converter and is converted into photoneutrons to form a photoneutron beam by the photoneutron enhancement chamber and a beam-limited channel connected with the photoneutron enhancement chamber.

In a preferred embodiment of the invention, the X-ray beam transmits through the inspected object, and is received by the X-ray detector array, the photoneutron beam transmits through the inspected object, and is received by the neutron detector array.

In a preferred embodiment of the invention, along the direction of scanning, an X-ray scanner frame comprising the X-ray beam and the X-ray detector array is preceding, a neutron scanner frame comprising photoneutron beams and the neutron detector array is behind, that is, the inspected object is scanned by X-ray scanner frame first, and then scanned by the neutron scanner frame.

In a preferred embodiment of the invention, the photoneutron converter comprises beryllium or other material, and has a shape of spherical dome, cylinder, cone, L-shaped plate or other shape.

In a preferred embodiment of the invention, between the photoneutrons emitting window of the photoneutron enhancement chamber and the beam-limited channel, a bismuth filter is interposed on the way of the photoneutron beam.

In a preferred embodiment of the invention, the photoneutron enhancement chamber comprises lead and graphite layers or other material.

Due to above technologies employed in this invention, the n-x curves are Z-dependence only and not related to the thickness of inspected objects. The invention has following advantages: compact equipment, high detecting efficiency. By this method that container is scanned by the X-ray scanner frame first and by the neutron scanner frame later, the affect on the X-ray transmission image by gamma ray induced by neutron activation is eliminated. By employing time-dividing technology, that is the delay of neutron beam emitting time relative to the emitting time of the Linac X-ray beam, the interfere of the neutrons with X-ray transmission image and the X-rays with neutron transmission image can be reduced, and the images quality can be improved. As the fan-shaped X-ray beam and the fan-shaped neutron bean are narrow-beam, the scattering interference can be reduced, easy to radiation protection and has high spatial resolution. In the case of fully-loaded container or thick objects inspection, the material discrimination can perform well. So it can be used to detect explosive, drug, contraband, special nuclear material, radiation material and other material in container, container truck, railcar or other voluminous objects.

DETAILED DESCRIPTION OF THE PREFERRED EMBODIMENTS

Hereinafter, the embodiments of the invention will be described with the accompanying drawings. For convenience's sake, such components in FIGS. 1-3 will be indicated with the same or similar reference numerals.

[Configuration]

Figure 1:
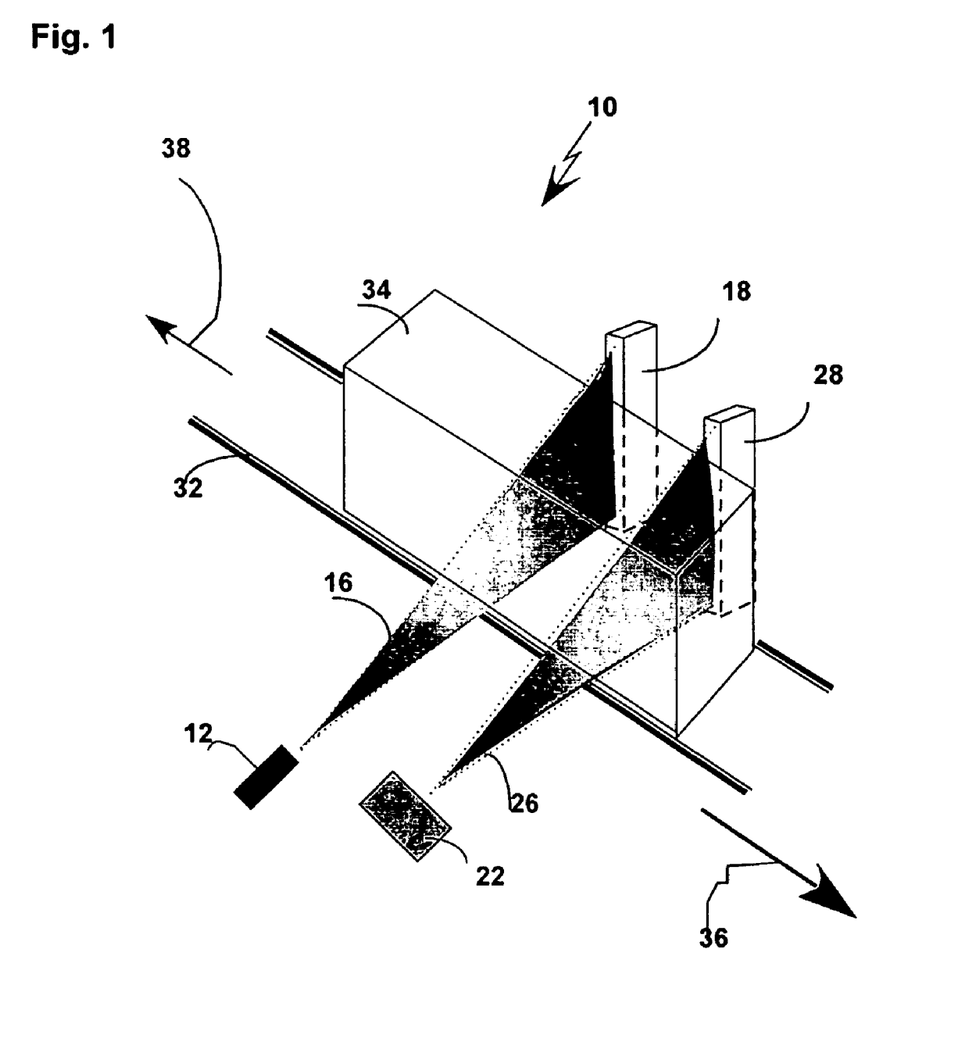
FIG. 1 is a schematic illustration showing the configuration of one equipment according to an embodiment of the invention.

FIG. 1 is a schematic illustration showing the configuration of one equipment according to an embodiment of the invention.

Referring to FIG. 1, the equipment 10 according to the first embodiment of the invention comprises a container convey track 32, at least one inspected containers or other voluminous objects 34 that can be placed on the container convey track 32, a fast neutron source 12 for producing neutrons, a continuous spectral X-ray source 22 for producing X-rays, a neutron detector array 18 having a high detecting efficiency with respect to neutron, an X-ray detector array 28 having a high detecting efficiency with regard to X-ray, a fan-shaped neutron beam 16 and a fan-shaped X-ray beam 26.

The fast neutron source 12 is one of a neutron generator and isotope neutron source. The continuous spectral X-ray source 22 is one of an electron linear accelerator (Linac) and an X-ray machine. The fast neutron source 12 and the continuous spectral X-ray source 22 are located at one side of the container convey track 32. The neutron detector array 18 and the X-ray detector array 28 are located at opposite side of the container convey track 32.

The neutrons emitted from the fast neutron source 12 are collimated into a fan-shaped neutron beam 16 which transmits through container 34 and then is received by the neutron detector array 18. The X-rays emitted from continuous spectral X-ray source 22 is collimated into a fan-shaped X-ray beam 26 which transmits through container 34 and then is received by the X-ray detector array 28.

A neutron scanner frame formed by the fast neutron source 12 and the neutron detector array 18 is located in parallel with an X-ray scanner frame formed by the continuous spectral X-ray source 22 and the X-ray detector array 28 and they move along the container convey track 32. The direction of scanning 36 is opposite to the moving direction 38 of the inspected container 34. Along the direction of scanning, the X-ray scanner frame is preceding, and the neutron scanner frame is behind. That is, the inspected container 34 is scanned by the X-ray scanner frame first, and then scanned by the neutron scanner frame.

Figure 2:
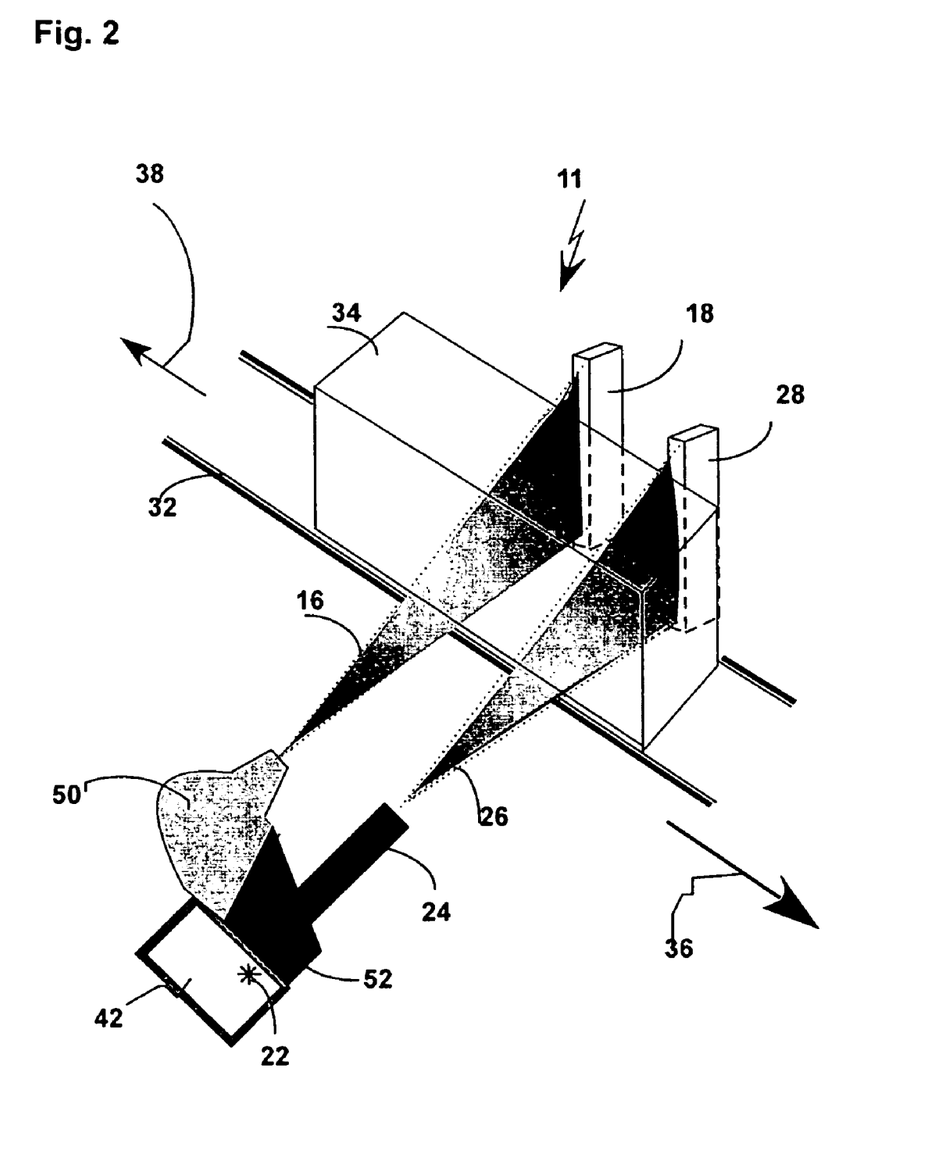
FIG. 2 is a schematic illustration showing the configuration of another equipment according to another embodiment of the invention.
Figure 3:
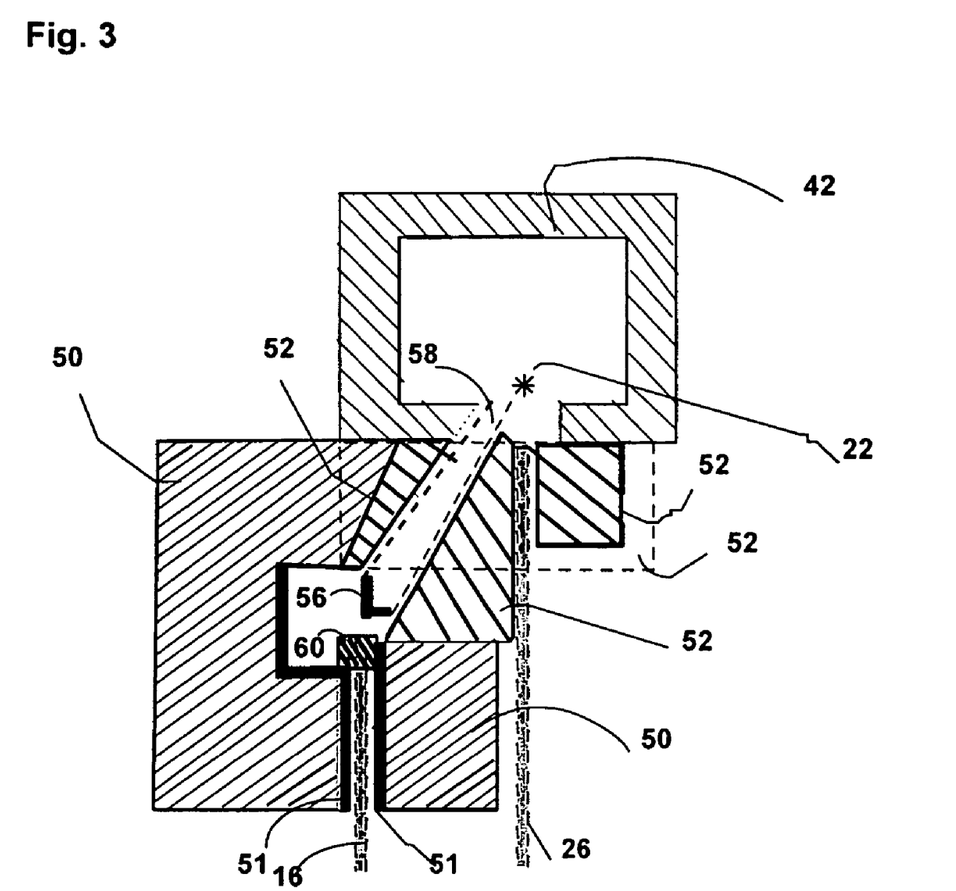
FIG. 3 is a schematic illustration showing the structure of the X-ray beam distributing collimator and photoneutron converting and enhancing facility.

FIG. 2 is a schematic illustration showing the configuration of another equipment according to another embodiment of the invention, and FIG. 3 is a schematic illustration showing the structure of the X-ray beam distributing collimator and photoneutron converting and enhancing facility.

Referring to FIG. 2 and FIG. 3, another equipment 11 according to the second embodiment of the invention comprises a container convey track 32, at least one inspected container or other voluminous object 34 that can be placed on the container convey track 32, an accelerator 42 which can produce continuous spectral X-ray beam and part of which is converted into photoneutrons, a neutron detector array 18 and an X-ray detector array 28.

Accelerator 42 is located at one side of the container convey track 32. The neutron detector array 18 and the X-ray detector array 28 are located at another side of the container convey track 32. A special designed X-ray distribution collimator 52 is installed at the X-ray beam emitting window of the accelerator 42. And the X-ray distribution collimator 52 divides the X-ray beam produced by the accelerator into two beams: one beam is collimated by the X-ray beam-limited collimator 24 so as to form a fan-shaped continuous spectral X-ray beam 26; the other beam 58 is collimated and leaded into a photoneutron enhancement chamber 50 which is made of lead, graphite layers or other materials.

A photoneutron converter 56 comprising beryllium or other material, and having a shape of spherical dome, cylinder, cone, L-shaped plate or other shape is placed in the photoneutron enhancement chamber 50, and is interposed in the path of the X-ray beam 58. The X-ray beam 58 impinges on the photoneutron converter 56 and is converted into photoneutrons to form a fan-shaped photoneutron beam 16 by the photoneutron enhancement chamber 50 and a neutron beam-limited channel 51 connected with the photoneutron enhancement chamber 50. Between the photoneutrons emitting window of the photoneutron enhancement chamber 50 and the neutron beam-limited channel 51, a bismuth cylinder filter 60 is interposed on the way of the photoneutron beam.

The fan-shaped photoneutron beam 16 aims at the neutron detector array 18 located on the other side of the container convey track 32, and the phothneutron beam 16 and the neutron detector array 18 form a neutron scanner frame. The fan-shaped X-ray beam 26 aims at the X-ray detector array 28 located on the other side of the container convey track 32, and the X-ray beam 26 and X-ray detector array 28 form an X-ray scanner frame.

Along the direction of scanning 36, the X-ray scanner frame is preceding, and the neutron scanner is behind. That is, the container 34 is scanned by the X-ray scanner frame first, and then scanned by the neutron scanner frame.

[Operation]

(a) A neutron scanner frame composed of the neutron source 12 and the neutron detector array 18 is located in parallel with an X-ray scanner frame composed of the X-ray source 22 and the X-ray detector array 28 and they move along the convey track. The inspected container 34 passes through X-ray scanner frame first, and then passes through the neutron scanner frame. The fan-shaped X-ray beam 26 transmits through the inspected container 34. The transmitted beam is received by the X-ray detector array 28, and then forms a 2-dimensional X-ray transmission image. At the same scan, the fan-shaped neutron beam 16 transmits through the inspected container 34. The transmitted beam is received by the neutron detector array 18, and then forms a 2-dimensional neutron transmission image. If a pulse neutron source is used as the neutron source 12, the neutron source 12 and Linac X-ray source 22 are pulsed in synchronism, and the emitting time of pulse neutron source is delayed a period of time from the emitting time of the Linac pulse continuous spectral X-ray source.

(b) The materials discrimination method is implemented by employing Z-dependence n-x curves. The count $T_n$ of every neutron detector is the neutron intensity of the neutron transmitted through the container 34. The count $T_x$ of every X-ray detector is the X-ray intensity of the X-ray transmitted through the container 34. Using $c_1=f_1(T_x)$ as x-coordinator and $C_2=f_2(T_n,T_x)$ as y-coordinator, the pairs of $(c_1,c_2)$ compose the Z-dependence curves, which are employed to identify different material. Here, $f_1(T_x)$ denotes a function of the attenuation of X-ray, and $f_2(T_n,T_x)$ denotes a function of the attenuation difference of neutron and X-ray. One pixel value of neutron transmission image can be paired with the mean of one or several pixels value of the X-ray transmission image, and compose a $(c_1,c_2)$ pair on the Z-dependence curves, which are employed for material discrimination. Different materials are displayed by different colors in a material discrimination image.

The physics principle of the Z-dependence curve will be described as below.

The attenuation of narrow-beam monoenergetic neutrons transmitted through an irradiated object with thickness x(cm) can be calculated using the equation (1):

$$I_n = I_{n0} \exp(-\mu_n(Z, E) \cdot X) \quad (1)$$

where $I_n$ and $I_{n0}$ denote the measured intensities with and without attenuation respectively; $\mu_n(Z,E)$ denotes the linear attenuation coefficient (cm$^{-1}$) of irradiated object's material for neutrons, which is the function of effective atomic number Z of the object under inspection and the energy of incident neutrons E(MeV).

In case of narrow-beam continuous spectral neutrons, the attenuation of narrow-beam continuous spectral neutrons transmitted through an irradiated object with thickness x(cm) can be calculated using the equation (2):

$$I_n = \int_0^{E_{nb}} I_{n0}(E) \exp(-\mu_n(Z, E) \cdot x) dE \quad (2)$$

where $I_n$ denotes the measured intensity of transmitted neutrons; $I_{n0}(E)$ denotes the measured incident intensity of continuous spectral neutrons with boundary energy $E_{nb}$ (MeV); $\mu_n(Z,E)$ denotes the sum of linear attenuation coefficients (cm$^{-1}$) of irradiated object's material for neutrons, which is the function of effective atomic number Z of the object under inspection and the energy of incident neutrons E(MeV).

In the case of narrow-beam continuous spectral X-ray, the attenuation of the narrow-beam continuous spectral X-ray transmitted through an irradiated object with thickness x(cm) can be calculated using the equation (3):

$$I_x = \int_0^{E_{xb}} I_{x0}(E) \exp(-\mu_x(Z, E) \cdot x) dE \quad (3)$$

where $I_x$ denotes the measured intensity of transmitted X-ray; $I_{x0}(E)$ denotes the measured intensity of incident continuous spectral X-ray with boundary energy $E_{xb}$(MeV); $\mu_x(Z,E)$ denotes the sum of linear attenuation coefficients (cm$^{-1}$) of irradiated object's material for X-rays, which is the function of effective atomic number Z of the object under inspection and the energy of incident X-rays E(MeV).

In the case of both the neutron beam and the X-ray beam are continuous spectral distributions, the following nonlinear integration equation set (4) is employed to do material discrimination:

$$\begin{cases} T_n(E, x, Z) = \dfrac{\int_0^{E_{nb}} I_{n0}(E) e^{-\mu_n(E,Z)x} dE}{\int_0^{E_{nb}} I_{n0}(E) dE} \\ T_x(E, x, Z) = \dfrac{\int_0^{E_{xb}} I_{x0}(E) e^{-\mu_x(E,Z)x} dE}{\int_0^{E_{xb}} I_{x0}(E) dE} \end{cases} \quad (4)$$

where $T_n(E,x,Z)$ denotes the transparency of the irradiated object with effective atomic number Z and thickness x(cm) for flux of neutrons with boundary energy $E_{nb}$ (MeV); $I_{n0}(E)$ denotes the intensity of incident neutrons with energy E(MeV); $\mu_n(Z,E)$ denotes the sum of linear attenuation coefficients (cm$^{-1}$) of irradiated object's material for neutrons, which is the function of effective atomic number Z of the irradiated object and the energy of incident neutrons E(MeV); $T_x(E,x,Z)$ denotes the transparency of the irradiated object with effective atomic number Z and thickness x(cm) for flux of X-rays with boundary energy $E_{xb}$(MeV); $I_{x0}(E)$ denotes the intensity of incident X-ray with energy E(MeV); $\mu_x(Z,E)$ denotes the sum of linear attenuation coefficients (cm$^{-1}$) of irradiated material for X-rays, which is the function of effective atomic number Z of the object under inspection and the energy of incident X-rays with energy E(MeV).

In case of the neutron beam 16 is monoenergetic and the X-ray beam 26 is continuous spectral distribution, the following nonlinear integration equation set (5) is employed to do material discrimination:

$$\begin{cases} T_n(E_n, x, Z) = I_{n0}(E) e^{-\mu_n(E_n, Z)x} \\ T_x(E, x, Z) = \dfrac{\int_0^{E_{xb}} I_{x0}(E) e^{-\mu_x(E,Z)x} dE}{\int_0^{E_{xb}} I_{x0}(E) dE} \end{cases} \quad (5)$$

where $T_n(E,x,Z)$ denotes the transparency of the irradiated object with effective atomic number Z and thickness x(cm) for flux of neutrons with energy E(MeV); $I_{n0}(E)$ denotes the intensity of incident neutron with energy E(MeV); $\mu_n(Z,E)$ denotes the linear attenuation coefficient (cm$^{-1}$) of irradiated object's material for neutrons, which is the function of effective atomic number Z of the object under inspection and the energy of incident neutrons E(MeV); $T_x(E,x,Z)$ denotes the transparency of the irradiated object with effective atomic number Z and thickness x(cm) for flux of X-rays with boundary energy $E_{xb}$(MeV); $I_{x0}(E)$ denotes the intensity of incident X-ray with energy E(MeV); $\mu_x(Z,E)$ denotes the sum of linear attenuation coefficients (cm$^{-1}$) of irradiated material for X-rays, which is the function of effective atomic number Z of the object under inspection and the energy of incident X-rays with energy E(MeV).

The solutions of equation set (4) or (5) are not related to the thickness of the irradiated object, but only are Z-dependency. So it can be used for material discrimination.

In present invention, there are two scanning models: One is neutron scanner frame and X-ray scanner frame moving, while the inspected object 34 holds still. The other is the inspected object 34 moving along the convey track 32, while the neutron scanner frame and X-ray scanner frame are stationary.

It is to be understood that the present invention may be carried out in any other manner than specifically described above as embodiments, and many modifications and variations are possible within the scope of the invention.

What is claimed is:

1. A method of discriminating materials by employing fast neutron and continuous spectral X-ray comprising the steps of:
   (a) transmitting a fast neutron beam produced by a fast neutron source and a continuous spectral X-ray beam produced by a continuous spectral X-ray source through inspected object;
   (b) directly measuring the intensity of the transmitted X-rays and the intensity of the transmitted neutrons by an X-ray detector array and a neutron detector array respectively; and
   (c) identifying the materials of the inspected object by Z-dependency curves formed by the attenuation differences between the neutron beam and the X-ray beam transmitted through different materials of the inspected object.

2. The method according to claim 1, further comprising a step of:
   (d) forming 2-dimensional X-ray transmission image and neutron transmission image at same scan.

3. The method according to claim 1, wherein the fast neutron source is one of a neutron generator, an isotope neutron source and a photoneutron source; and
   the continuous spectral X-ray source is one of an electron linear accelerator and an X-ray machine.

4. The method according to claim 3, the photoneutron source is an accelerator for producing an X-ray beam part of which impinges on photoneutron converter and is converted into photoneutrons.

5. The method according to claim 4, wherein
   a distribution collimator divides the X-ray beam produced by the accelerator into two beams, one beam is collimated by an X-ray beam-limited collimator so as to form an X-ray beam, the other beam impinges on photoneutron converter and is convened into photoneutrons to form a photoneutron beam by beam-limited collimator.

6. The method according to claim 1, wherein,
   the fast neutron beam and the continuous spectral X-ray beam are measured by an X-ray detector away having high X-ray detecting efficiency and a neutron detector away having high neutron detecting efficiency respectively.

7. The method according to claim 6, wherein along the scanning tunnel a neutron scanner frame comprising the fast neutron source and the neutron detector array is located in parallel with an X-ray scanner frame comprising the X-ray source and the X-ray detector array.

8. The method according to claim 7, wherein
   along the direction of scanning, the X-ray scanner frame is preceding and the neutron scanner frame is behind so that the inspected object is scanned by X-ray scanner frame first, and then scanned by neutron scanner frame.

9. The method according to claim 8, wherein
   the neutron source and the X-ray source are pulsed in synchronism, and the emitting time of pulse neutron source is delayed a period of time from the emitting time of the pulse X-ray source.

10. The method according to claim 1, wherein the identifying of the materials comprising: measuring the intensity $T_n$ of neutron transmitted through the inspected object by every neutron detector of the neutron detector array;
    measuring the intensity $T_x$ of X-ray transmitted through the inspected object by every X-ray detector in the X-ray detector array;
    composing Z-dependence curves by the pairs of $(c_1, c_2)$, wherein $c_1 = f_1(T_x)$ is used as x-coordinator and $c_2 = f_2(T_n, T_x)$ is used as y-coordinator, wherein $f_1(T_x)$ denotes a function of the attenuation of X-ray, and $f_2(T_n, T_x)$ denotes a function of the attenuation difference of neutron and X-ray;
    identifying the different materials of the inspected object by using the Z-dependence curves; and
    displaying the identified different materials by different colors in an material discrimination image.

11. The method according to claim 10, wherein
    one pixel value of the neutron transmission image is paired with the mean of one or several pixels value of the X-ray transmission image to compose a $(c_1, c_2)$ pair on one of the Z-dependence curves.

12. The method according to claim 11, wherein there are two scanning models for forming the X-ray transmission image and the neutron transmission image, one is the neutron scanner frame and the X-ray scanner frame moving, while the inspected object holds still; the other is the inspected object moving along the scanning tunnel, while the neutron scanner frame and the X-ray scanner frame are stationary.

13. An equipment for discriminating materials by employing fast neutron and continuous spectral X-ray, comprising:
    a fast neutron source for producing neutrons to transmit through an inspected object;
    a continuous spectral X-ray source for producing X-rays to transmit through the inspected object;
    a neutron detector away for detecting the intensity of the transmitted neutrons; and
    an X-ray detector away for detecting the intensity of the transmitted X-rays;
    wherein the fast neutron source and the continuous spectral X-ray source are located at one side of a scanning tunnel, and the neutron detector array and the X-ray detector array are located at an opposite side of the scanning tunnel;
    the equipment further comprises means for identifying the materials of the inspected object by Z-dependency curves formed by the attenuation differences between the neutron beam and the X-ray beam transmitted through different materials of the inspected object.

14. The equipment according to claim 13, wherein
the X-rays produced by the X-ray source are collimated into an X-ray beam which aims at the X-ray detector array, the X-ray beam transmits through the inspected object, and is received by the X-ray detector array;
the neutrons produced by the fast neutron source are collimated into a neutron beam which aims at the neutron detector array, the neutron beam transmits through the inspected object, and is received by the neutron detector array.

15. The equipment according to claim 13, wherein
the fast neutron source is one of a neutron generator, an isotope neutron source and a photoneutron source; and
the continuous spectral X-ray source is one of an electron linear accelerator and an X-ray machine.

16. The equipment according to claim 13, wherein
along the scanning tunnel, a neutron scanner frame comprising the fast neutron source and the neutron detector array is located in parallel with an X-ray scanner frame comprising the X-ray source and the X-ray detector array.

17. The equipment according to claim 16, wherein
along the direction of scanning, the X-ray scanner frame is preceding, the neutron scanner frame is behind so that the inspected object is scanned by the X-ray scanner frame first, and then scanned by the neutron scanner frame.

18. An equipment for discriminating materials by employing fast neutron and continuous spectral X-ray, comprising:
an accelerator producing continuous spectral X-rays and photoneutrons to transmit through inspected object;
a neutron detector away for detecting the intensity of the transmitted photoneutrons; and
an X-ray detector away for detecting intensity of the transmitted X-rays;
wherein the accelerator is located at one side of a scanning tunnel, the neutron detector array and the X-ray detector array are located at the other side of the scanning tunnel;
the equipment further comprises means for identifying the materials of the inspected object by Z-dependency curves formed by the attenuation differences between the photoneutron beam and the X-ray beam transmitted through different materials of the inspected object.

19. The equipment according to claim 18, further comprising:
an X-ray distribution collimator, which is installed at an X-ray beam emitting window of the accelerator, and divides the X-ray beam into two beams, one beam is collimated by the X-ray beam-limited collimator so as to form an X-ray beam, the other beam is collimated and leaded into a photoneutron enhancement chamber.

20. The equipment according to claim 19, further comprising:
a photoneutron converter, which is placed in the photoneutron enhancement chamber, and is interposed in the path of the X-ray beam, the X-ray beam impinges on the photoneutron converter and is converted into photoneutrons to form a photoneutron beam by the photoneutron enhancement chamber and a beam-limited channel connected with the photoneutron enhancement chamber.

21. The equipment according to claim 20, wherein
the X-ray beam transmits through the inspected object, and is received by the X-ray detector array, the photoneutron beam transmits through the inspected object, and is received by the neutron detector array.

22. The equipment according to claim 21, wherein
along the direction of scanning, an X-ray scanner frame comprising X-ray beam and the X-ray detector array is preceding, a neutron scanner frame comprising photoneutron beams and the neutron detector away is behind so that the inspected object is scanned by X-ray scanner frame first, and then scanned by the neutron scanner frame.

23. The equipment according to claim 20, wherein
the photoneutron converter comprises beryllium or other material, and has a shape of spherical dome, cylinder, cone, L-shaped plate or other shape.

24. The equipment according to claim 20, wherein
between the photoneutrons emitting window of the photoneutron enhancement chamber and the beam-limited channel, a bismuth filter is interposed on the way of the photoneutron beam.

25. The equipment according to claim 20, wherein
the photoneutron enhancement chamber comprises lead and graphite layers or other material.

* * * * *

UNITED STATES PATENT AND TRADEMARK OFFICE
CERTIFICATE OF CORRECTION

PATENT NO. : 7,399,976 B2
APPLICATION NO. : 11/353472
DATED : July 15, 2008
INVENTOR(S) : Kejun Kang et al.

It is certified that error appears in the above-identified patent and that said Letters Patent is hereby corrected as shown below:

Col. 9, line 63, change "convened" to --converted--.

Col. 9, line 67, change "away" to --array--.

Col. 10, line 2, change "away" to --array--.

Col. 11, line 31, change "away" to --array--.

Col. 11, line 33, change "away" to --array--.

Col. 12, line 26, change "away" to --array--.

Signed and Sealed this

Fourth Day of August, 2009

JOHN DOLL
*Acting Director of the United States Patent and Trademark Office*